US012458545B2

(12) United States Patent
Gao et al.

(10) Patent No.: US 12,458,545 B2
(45) Date of Patent: Nov. 4, 2025

(54) PANT-TYPE ABSORBENT ARTICLE AND MANUFACTURING METHOD THEREOF

(71) Applicant: The Procter & Gamble Company, Cincinnati, OH (US)

(72) Inventors: Xu Gao, Beijing (CN); Masayuki Tsuji, Kakogawa (JP); Koichi Morimoto, Beijing (CN); Ling Tong, Beijing (CN); Abhishek Surushe, Kelkheim (DE)

(73) Assignee: The Procter & Gamble Company, Cincinnati, OH (US)

( * ) Notice: Subject to any disclaimer, the term of this patent is extended or adjusted under 35 U.S.C. 154(b) by 363 days.

(21) Appl. No.: 17/875,476

(22) Filed: Jul. 28, 2022

(65) Prior Publication Data

US 2022/0362070 A1 Nov. 17, 2022

Related U.S. Application Data

(63) Continuation of application No. PCT/CN2021/077842, filed on Feb. 25, 2021.

(30) Foreign Application Priority Data

Feb. 28, 2020 (WO) ................ PCT/CN2020/077152
Jul. 24, 2020 (WO) ................ PCT/CN2020/104295

(51) Int. Cl.
*A61F 13/49* (2006.01)
*A61F 13/15* (2006.01)
(Continued)

(52) U.S. Cl.
CPC .. *A61F 13/49011* (2013.01); *A61F 13/15593* (2013.01); *A61F 13/15699* (2013.01);
(Continued)

(58) Field of Classification Search
CPC .. A61F 13/49466; A61F 13/494–49473; A61F 13/49
See application file for complete search history.

(56) References Cited

U.S. PATENT DOCUMENTS 4,938,755 A * 7/1990 Foreman ........... A61F 13/49466 604/385.27
5,030,303 A 7/1991 Cucuzza
(Continued)

FOREIGN PATENT DOCUMENTS

CN 1282234 A 1/2001
CN 1784192 A 6/2006
(Continued)

OTHER PUBLICATIONS

AA01455FQ PCT Search Report and Written Opinion for PCT/CN2021/077842 dated May 28, 2021, 12 pages.
(Continued)

*Primary Examiner* — Nicholas J. Weiss
*Assistant Examiner* — Linnae E. Raymond
(74) *Attorney, Agent, or Firm* — Charles R. Matson

(57) ABSTRACT

A pant type absorbent article includes a back elastic belt comprising a waist guard portion extending towards the crotch region from a closed base line towards an open edge, wherein the waist guard portion is formed by a first inner waist fold extending from a second inner waist fold, the second inner waist fold extending from the inner sheet, and a first elastic member bonded between the first inner waist fold and the second inner waist fold, wherein the waist guard portion is partially bonded to the remainder of the elastic belt from which the first and second inner waist folds extend to define a pocket.

8 Claims, 10 Drawing Sheets

(51) Int. Cl.

| | |
|---|---|
| ***A61F 13/494*** | (2006.01) |
| ***A61F 13/496*** | (2006.01) |
| ***A61F 13/53*** | (2006.01) |
| ***A61F 13/84*** | (2006.01) |

(52) U.S. Cl.

CPC .. *A61F 13/49012* (2013.01); *A61F 13/49014* (2013.01); *A61F 13/49453* (2013.01); *A61F 13/49466* (2013.01); *A61F 13/496* (2013.01); *A61F 13/4963* (2013.01); *A61F 13/53* (2013.01); *A61F 2013/15325* (2013.01); *A61F 2013/15365* (2013.01); *A61F 2013/49028* (2013.01); *A61F 2013/49033* (2013.01); *A61F 2013/49038* (2013.01); *A61F 2013/49076* (2013.01); *A61F 2013/49092* (2013.01); *A61F 2013/8402* (2013.01)

(56) References Cited

U.S. PATENT DOCUMENTS

| | | | |
|---|---|---|---|
| 5,569,227 | A | 10/1996 | Vandemoortele et al. |
| 5,904,675 | A | 5/1999 | Laux |
| 8,518,010 | B2 | 8/2013 | Kuwano et al. |
| 8,939,956 | B2 | 1/2015 | Mukai |
| 9,023,006 | B2 | 5/2015 | Takino et al. |
| 9,107,778 | B2 | 8/2015 | Sasayama et al. |
| 10,406,040 | B2 | 9/2019 | Chatterjee |
| 11,607,350 | B2 | 3/2023 | Morimoto et al. |
| 2002/0045876 | A1 | 4/2002 | Suzuki |
| 2002/0058922 | A1 | 5/2002 | Skog |
| 2002/0120248 | A1 | 8/2002 | Onishi et al. |
| 2002/0183706 | A1* | 12/2002 | Valentin ............ A61F 13/49466 604/394 |
| 2003/0114819 | A1 | 6/2003 | Sayama et al. |
| 2003/0230378 | A1 | 12/2003 | Olsson et al. |
| 2007/0123834 | A1 | 5/2007 | Mcdowall et al. |
| 2010/0318054 | A1 | 12/2010 | Langdon et al. |
| 2012/0311770 | A1 | 12/2012 | Nakajima |
| 2013/0310797 | A1 | 11/2013 | Zink |
| 2014/0031782 | A1 | 1/2014 | Ichikawa et al. |
| 2015/0173973 | A1 | 6/2015 | Lavon et al. |
| 2015/0182388 | A1 | 7/2015 | Katsuragawa et al. |
| 2015/0320612 | A1 | 11/2015 | Seitz |
| 2016/0270975 | A1 | 9/2016 | Surushe et al. |
| 2016/0270977 | A1 | 9/2016 | Surushe et al. |
| 2016/0270979 | A1 | 9/2016 | Raycheck et al. |
| 2016/0287449 | A1* | 10/2016 | Surushe ............ A61F 13/49413 |
| 2017/0000658 | A1 | 1/2017 | Chatterjee |
| 2017/0143560 | A1 | 5/2017 | Morimoto et al. |
| 2017/0246055 | A1 | 8/2017 | Barnes |
| 2018/0071155 | A1 | 3/2018 | Bishop |
| 2018/0104116 | A1 | 4/2018 | Bishop et al. |
| 2018/0221219 | A1 | 8/2018 | Morimoto et al. |
| 2018/0289562 | A1 | 10/2018 | Inoue |
| 2019/0350771 | A1 | 11/2019 | Chatterjee |
| 2020/0197560 | A1 | 6/2020 | Buchalter |
| 2021/0093193 | A1 | 4/2021 | Birkner |
| 2021/0100695 | A1* | 4/2021 | Ishibashi ........... A61F 13/49015 |
| 2021/0113388 | A1 | 4/2021 | Matsui |
| 2021/0267815 | A1 | 9/2021 | Gao et al. |
| 2022/0339044 | A1 | 10/2022 | Surushe et al. |
| 2022/0362068 | A1 | 11/2022 | Luan et al. |
| 2022/0362069 | A1 | 11/2022 | Gao et al. |
| 2024/0082073 | A1 | 3/2024 | Mun |

FOREIGN PATENT DOCUMENTS

| | | | | | |
|---|---|---|---|---|---|
| CN | 1903152 | A | | 1/2007 | |
| CN | 101785729 | A | | 7/2010 | |
| CN | 103282000 | A | | 9/2013 | |
| CN | 104349756 | A | | 2/2015 | |
| CN | 205054607 | U | | 3/2016 | |
| CN | 107405232 | A | | 11/2017 | |
| CN | 107427395 | A | | 12/2017 | |
| CN | 107427403 | A | | 12/2017 | |
| CN | 107820419 | A | | 3/2018 | |
| CN | 107920934 | A | | 4/2018 | |
| CN | 108093621 | A | | 5/2018 | |
| CN | 108601690 | A | | 9/2018 | |
| CN | 109758299 | A | | 5/2019 | |
| CN | 109982669 | A | | 7/2019 | |
| CN | 110290772 | A | | 9/2019 | |
| EP | 2529717 | A1 | | 12/2012 | |
| EP | 3162337 | A1 | * | 5/2017 | ............. A61F 13/15 |
| EP | 3287108 | A1 | | 2/2018 | |
| EP | 3351227 | A1 | | 7/2018 | |
| JP | 07184955 | A | | 7/1995 | |
| JP | H08154971 | A | | 6/1996 | |
| JP | 2001212176 | A | | 8/2001 | |
| JP | 2001252303 | A | | 9/2001 | |
| JP | 2006263306 | A | * | 10/2006 | |
| JP | 2008237391 | A | | 10/2008 | |
| JP | 2009207778 | A | | 9/2009 | |
| JP | 2009219627 | A | | 10/2009 | |
| JP | 2011156110 | A | | 8/2011 | |
| JP | 2016112208 | A | | 6/2016 | |
| JP | 3211442 | U | | 6/2017 | |
| JP | 2018061839 | A | | 4/2018 | |
| JP | 2018082865 | A | | 5/2018 | |
| JP | 2018104116 | A | | 7/2018 | |
| JP | 2018108337 | A | | 7/2018 | |
| JP | 2018118093 | A | | 8/2018 | |
| JP | 2019115461 | A | | 7/2019 | |
| JP | 2020135072 | A | | 8/2020 | |
| WO | WO-0072791 | A1 | * | 12/2000 | ....... A61F 13/49466 |
| WO | 2006017718 | A1 | | 2/2006 | |
| WO | 2009084643 | A1 | | 7/2009 | |
| WO | 2011087503 | A1 | | 7/2011 | |
| WO | 2012105212 | A1 | | 8/2012 | |
| WO | 2016029655 | A1 | | 3/2016 | |
| WO | 2016159983 | A1 | | 10/2016 | |
| WO | 2016170909 | A1 | | 10/2016 | |
| WO | 2017003423 | A1 | | 1/2017 | |
| WO | WO-2017141808 | A1 | * | 8/2017 | ........... A61F 13/494 |
| WO | 2018123154 | A1 | | 7/2018 | |
| WO | WO-2018152834 | A1 | * | 8/2018 | ............. A61F 13/49 |
| WO | 2019038956 | A1 | | 2/2019 | |
| WO | WO-2019073684 | A1 | * | 4/2019 | ............. A61F 13/49 |
| WO | 2021168782 | A1 | | 9/2021 | |
| WO | 2021170026 | A1 | | 9/2021 | |

OTHER PUBLICATIONS

All Office Actions; U.S. Appl. No. 17/875,471, filed on Jul. 28, 2022.

All Office Actions; U.S. Appl. No. 17/875,463, filed on Jul. 28, 2022.

Unpublished U.S. Appl. No. 17/875,463, filed on Jul. 28, 2022, to Lan Luan et al.

Unpublished U.S. Appl. No. 17/875,471, filed on Jul. 28, 2022, to Xu Gao et al.

All Office Actions, U.S. Appl. No. 17/180,978, filed on Feb. 22, 2021.

All Office Actions; U.S. Appl. No. 19/205,029, filed on May 12, 2025.

U.S. Unpublished U.S. Appl. No. 19/205,029, filed on May 12, 2025, to Xu Gao et al.

* cited by examiner

PANT-TYPE ABSORBENT ARTICLE AND MANUFACTURING METHOD THEREOF

CROSS REFERENCE TO RELATED APPLICATION

This application is a continuation of, and claims priority under 35 U.S.C. § 120 to, Patent Application No. PCT/CN2021/077842, filed on Feb. 25, 2021, which claims priority to Patent Application No. PCT/CN2020/077152, filed on Feb. 28, 2020 and Patent Application No. PCT/CN2020/104295, filed on Jul. 24, 2020, the entire disclosures of which are hereby incorporated by reference.

FIELD OF THE INVENTION

The present invention relates to pant-type absorbent articles having a protective measure for preventing leakage of low viscosity bodily exudates, while also maintaining other functions as a pant-type wearable article. The present invention also relates to methods of manufacturing such pant-type absorbent articles.

BACKGROUND OF THE INVENTION

Infants and other individuals wear absorbent articles such as diapers to receive and contain urine and other body exudates. Pull-on absorbent articles, or pant-type absorbent articles, such as described in PCT Publication WO 2006/17718A, are those which are donned by inserting the wearer's legs into the leg openings and sliding the article up into position about the lower torso. Pant-type absorbent articles have become popular for younger babies requiring a soft fit around the waist opening and leg openings. Pant-type absorbent articles have also become popular for females having heavy flow or overnight usage during menstruation periods. One function desired for a pant-type article is a protective measure for preventing leakage of low viscosity bodily exudates through the waist opening. Those pant-type articles having less material around the waist opening for breathability purpose or otherwise, may have risk of leakage from the waist opening, particularly when the wearer is lying on his/her back or belly.

Pant-type articles may take various structures wherein the circumference of the waist opening and vicinity thereof is made elastic enough to facilitate the wearer or the caregiver to expand the article and insert the wearer's legs into the leg openings for wearing the article. Accordingly, pant-type articles provide only a very small range of size adjustment or body configuration adjustment based on the structural limitations of the article. As such, pant-type articles are typically so configured to accommodate size and configuration ranges by providing the elastic belt region very stretchable and comfortable to wear, yet with reliable fit such that sufficient protection against sagging and leakage may be provided. It is desired that such basic functions of the elastic belt region may be maintained even with introduction of the aforementioned protective measure.

Based on the foregoing, there is a need for an absorbent article provided with a protective measure for preventing leakage of low viscosity bodily exudates from the waist opening, while maintaining good stretchability for ease of application, good fit for preventing sagging, good comfort and softness, and good breathability. There is also a need for providing such an absorbent article which can be economically made.

SUMMARY OF THE INVENTION

The present invention is directed to an absorbent article having a longitudinal direction and a transverse direction comprising a front elastic belt, a back elastic belt, a crotch region, a waist opening, and a pair of leg openings; the crotch region extending longitudinally between the front elastic belt and the back elastic belt; each of the front and back elastic belt is formed by an outer sheet, an inner sheet, and a second elastic member bonded between the outer sheet and the inner sheet, wherein the outer sheet is the garment-facing surface;

the absorbent article comprising an absorbent main body extending the entire longitudinal dimension of the crotch region and further extending partly into each of the front elastic belt and the back elastic belt, the absorbent main body comprising a liquid pervious topsheet, a liquid impervious backsheet, and an absorbent material region sandwiched therebetween;

wherein at least one of the front elastic belt and the back elastic belt comprise a waist guard portion extending towards the crotch region from a closed base line towards an open edge, wherein the waist guard portion is formed by a first inner waist fold extending from a second inner waist fold, the second inner waist fold extending from the inner sheet, and a first elastic member bonded between the first inner waist fold and the second inner waist fold, wherein the waist guard portion is partially bonded to the remainder of the elastic belt from which the first and second inner waist folds extend to define a pocket.

BRIEF DESCRIPTION OF THE DRAWINGS

While the specification concludes with claims particularly pointing out and distinctly claiming the subject matter which is regarded as forming the present invention, it is believed that the invention will be better understood from the following description which is taken in conjunction with the accompanying drawings and which like designations are used to designate substantially identical elements, and in which:

DEFINITIONS

Figure 1:
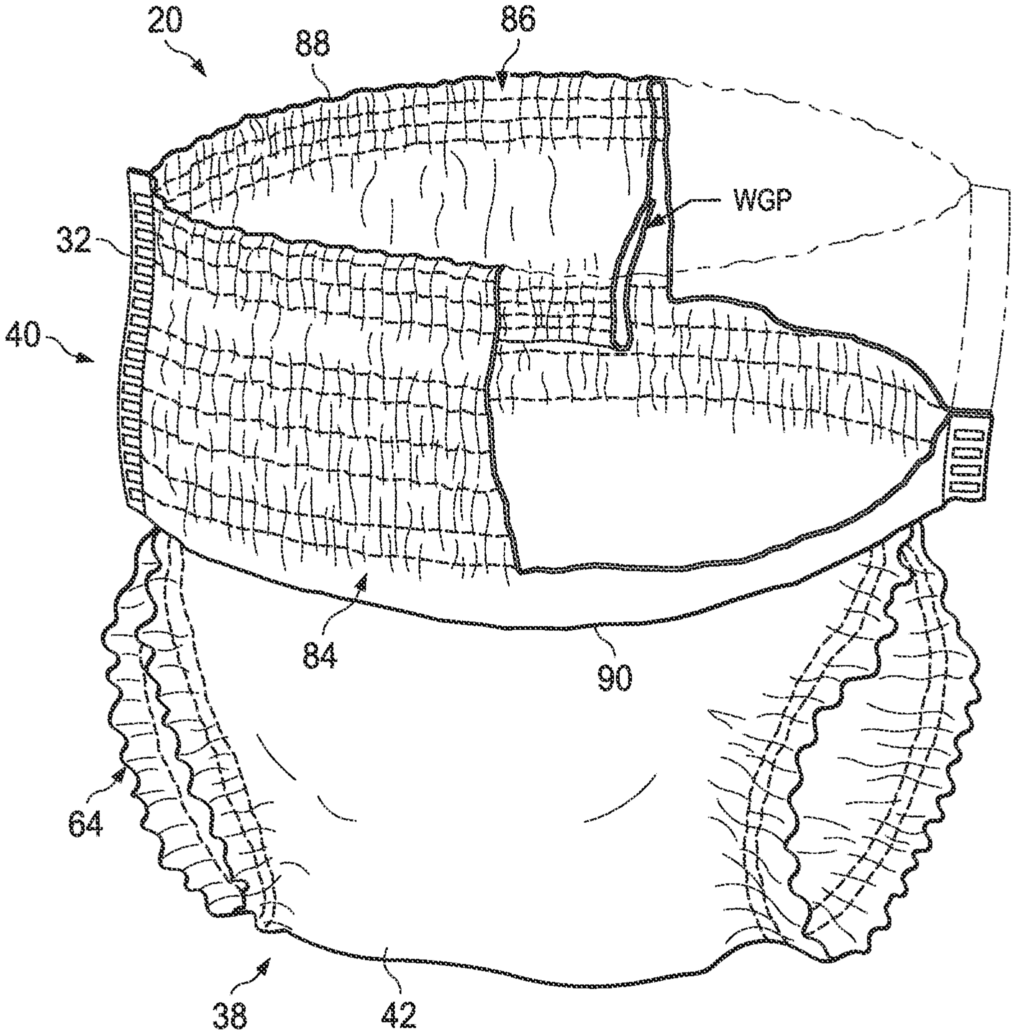
FIG. 1 is a perspective view of one embodiment of an absorbent article of the present invention.

As used herein, the following terms shall have the meaning specified thereafter:

"Absorbent article" refers to articles of wear which may be in the form of pants, taped diapers, incontinent briefs, feminine hygiene garments, and the like, so configured to also absorb and contain various exudates such as urine, feces, and menses discharged from the body. The "absorbent article" may serve as an outer cover adaptable to be joined with a separable disposable absorbent insert for providing absorbent and containment function, such as those disclosed in PCT publication WO 2011/087503A.

"Pant" refers to disposable absorbent articles having a pre-formed waist and leg openings. A pant may be donned by inserting a wearer's legs into the leg openings and sliding the pant into position about the wearer's lower torso. Pants are also commonly referred to as "closed diapers", "prefastened diapers", "pull-on diapers", "training pants" and "diaper-pants".

"Longitudinal" refers to a direction running substantially perpendicular from a waist edge to an opposing waist edge of the article and generally parallel to the maximum linear dimension of the article.

"Transverse" refers to a direction perpendicular to the longitudinal direction.

"Proximal" and "distal" refer respectively to the position closer or farther relative to the longitudinal center of the article.

"Inward" and "outward" refer respectively to the position closer or farther relative to the transverse center of the article.

"Body-facing", "inner", "garment-facing", and "outer" refer respectively to the relative location of an element or a surface of an element or group of elements. "Body-facing" and "inner" implies the element or surface is nearer to the wearer during wear than some other element or surface. "Garment-facing" and "outer" implies the element or surface is more remote from the wearer during wear than some other element or surface (i.e., element or surface is proximate to the wearer's garments that may be worn over the disposable absorbent article).

"Disposed" refers to an element being located in a particular place or position.

"Joined" refers to configurations whereby an element is directly secured to another element by affixing the element directly to the other element and to configurations whereby an element is indirectly secured to another element by affixing the element to intermediate member(s) which in turn are affixed to the other element.

"Film" refers to a sheet-like material wherein the length and width of the material far exceed the thickness of the material. Typically, films have a thickness of about 0.5 mm or less.

"Water-permeable" and "water-impermeable" refer to the penetrability of materials in the context of the intended usage of disposable absorbent articles. Specifically, the term "water-permeable" refers to a layer or a layered structure having pores, openings, and/or interconnected void spaces that permit liquid water, urine, or synthetic urine to pass through its thickness in the absence of a forcing pressure. Conversely, the term "water-impermeable" refers to a layer or a layered structure through the thickness of which liquid water, urine, or synthetic urine cannot pass in the absence of a forcing pressure (aside from natural forces such as gravity). A layer or a layered structure that is water-impermeable according to this definition may be permeable to water vapor, i.e., may be "vapor-permeable".

"Extendibility" and "extensible" mean that the width or length of the component in a relaxed state can be extended or increased.

"Elasticated" and "elasticized" mean that a component comprises at least a portion made of elastic material.

"Elongatable material", "extensible material", or "stretchable material" are used interchangeably and refer to a material that, upon application of a biasing force, can stretch to an elongated length of at least about 110% of its relaxed, original length (i.e. can stretch to 10 percent more than its original length), without rupture or breakage, and upon release of the applied force, shows little recovery, less than about 20% of its elongation without complete rupture or breakage as measured by EDANA method 20.2-89. In the event such an elongatable material recovers at least 40% of its elongation upon release of the applied force, the elongatable material will be considered to be "elastic" or "elastomeric." For example, an elastic material that has an initial length of 100 mm can extend at least to 150 mm, and upon removal of the force retracts to a length of at least 130 mm (i.e., exhibiting a 40% recovery). In the event the material recovers less than 40% of its elongation upon release of the applied force, the elongatable material will be considered to be "substantially non-elastic" or "substantially non-elastomeric". For example, an elongatable material that has an initial length of 100 mm can extend at least to 150 mm, and upon removal of the force retracts to a length of at least 145 mm (i.e., exhibiting a 10% recovery).

"Dimension", "Length", "Width", "Pitch", "Diameter", "Aspect Ratio", "Angle", and "Area" of the article are all measured in a state wherein the article is extended to the Full Stretch Circumference W1 according to the "Whole Article Force Measurement" herein, and utilizing a ruler or a loupe, unless specified otherwise.

DETAILED DESCRIPTION OF THE INVENTION

Figure 2A:
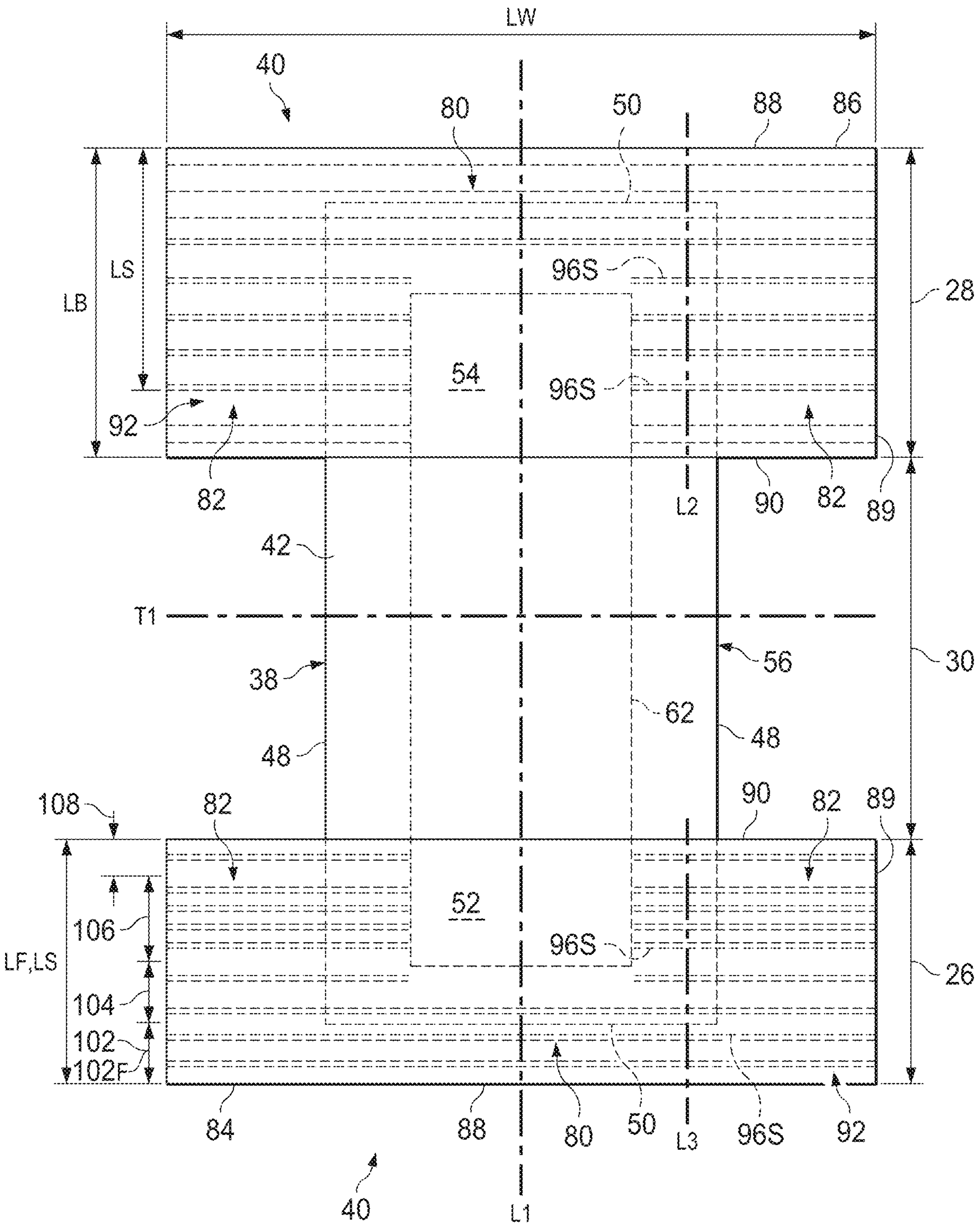
FIG. 2A is a schematic plan view of one embodiment of an absorbent article of the present invention with the seams unjoined and in a flat uncontracted condition showing the garment facing surface.

FIG. 1 is a perspective view of an absorbent article (20) of the present invention, and FIG. 2A is a schematic plan view of an absorbent article with the seams unjoined and in its flat uncontracted condition showing the garment-facing surface. The absorbent article (20) has a longitudinal centerline L1 which also serves as the longitudinal axis, and a transverse centerline T1 which also serves as the transverse axis. The absorbent article (20) has a body facing surface, a garment facing surface, a front elastic belt (84), a back elastic belt (86), a crotch region (30), and side seams (32) which join the front elastic belt (84) and the back elastic belt (86), to form two leg openings and a waist opening.

The absorbent article (20) may be a belt-type pant as in FIGS. 1 and 2A-2C comprising an absorbent main body (38) to cover the crotch region (30) of the wearer, a front elastic belt (84) and a back elastic belt (86) (hereinafter may be referred to as "front and back elastic belts"), the front and back elastic belts (84, 86) forming a discrete ring-like elastic belt (40) extending transversely defining the waist opening. For the belt-type pant, the discrete ring-like elastic belt (40) may also be referred to as the elastic belt (40). For the belt-type pant as in FIGS. 1 and 2A-2C, the front and back elastic belts (84, 86) and the absorbent main body (38) jointly define the leg openings. For the belt-type pant, the front elastic belt (84) is the front region (26), and the back elastic belt (86) is the back region (28), and the remainder is the crotch region (30). While not shown, the absorbent article (20) may be a uni-body type pant configured such that the outer cover layer of the absorbent main body (38) and the garment facing layer of the elastic belt (40) are common. For the uni-body type pant, the portion extending in the transverse direction between the side seams (32), respectively, are considered the front region (26) and the back region (28), and the remainder is the crotch region (30). For the uni-body type pant, the front region (26) is considered the front elastic belt (84), and the back region (28) is considered the back elastic belt (86).

The absorbent main body (38) comprises a topsheet, a backsheet and an absorbent material region (62) disposed between the topsheet and the backsheet. The absorbent main body (38) may further comprise an outer cover layer (42) for covering the garment-facing side of the backsheet. The topsheet may be a water permeable substrate. The backsheet may be a water impermeable film. The outer cover layer (42) may be a nonwoven sheet. The absorbent main body (38) comprises an absorbent material region (62) for absorbing and containing body exudates disposed on the absorbent main body (38), and an absorbent material non-existing region (61) surrounding the periphery of the absorbent material region (62). The area adjacent the front and back longitudinal end edges of the absorbent main body (38) comprise the backsheet. The absorbent material non-existing region (61) may be made of the topsheet and/or the backsheet and/or the outer cover layer (42) and/or other parts configuring the absorbent main body (38). In the embodiment shown in FIGS. 2A-2C, the absorbent main body (38) has a generally rectangular shape, left and right longitudinally extending side edges (48) and front and back transversely extending end edges (50). The absorbent material region (62) may exist through the entire longitudinal dimension of the crotch region and extending at least partly in the front and back regions (26, 28). The absorbent main body (38) may have a front waist panel (52) positioned in the front region (26) of the absorbent article (20), a back waist panel (54) positioned in the back region (28), and a crotch panel (56) between the front and back waist panels (52, 54) in the crotch region (30). The center of the front elastic belt (84) is joined to a front waist panel (52) of the absorbent main body (38), the center of the back elastic belt (86) is joined to a back waist panel (54) of the absorbent main body (38), the front and back elastic belts (84, 86) each having a left side panel and a right side panel (82) where the absorbent main body (38) does not overlap. The absorbent main body (38) has a crotch panel (56) positioned between the front waist panel (52) and the back waist panel (54).

The absorbent material region (62) may comprise an absorbent layer and an acquisition layer. The absorbent layer is the region wherein absorbent materials having a high retention capacity, such as superabsorbent polymers, are present. The absorbent layer may be substantially cellulose free. Superabsorbent polymers of the absorbent layer may be disposed between first and second layers of material immobilized by a fibrous layer of thermoplastic adhesive material. The first and second layers of materials may be nonwoven fibrous webs including synthetic fibers, such as mono-constituent fibers of PE, PET and PP, multiconstituent fibers such as side by side, core/sheath or island in the sea type fibers. Such synthetic fibers may be formed via a spunbonding process or a meltblowing process. The acquisition layer facilitates the acquisition and the distribution of body exudates and may be placed between the topsheet and the absorbent layer. The acquisition layer may include cellulosic fibers.

The absorbent layers may be disposed in plurality in the absorbent material region (62). Some portions of the absorbent layers may be configured to have substantially no absorbent material to form a channel or a plurality of channels. Channels may be useful for allowing the absorbent material region (62) to bend upon swelling with fluids, such that the absorbent article conforms to the wearer's body after swelling and prevent sagging of the article. The channels may also be formed in the acquisition layer, and may be configured to at least partly match the channels of the absorbent layer in the thickness direction.

Referring to FIG. 1, the absorbent main body (38) may comprise leg cuffs (64) made of material having high fluid impermeability, and elasticized to provide a barrier along both transverse edges of the absorbent main body (38). Such leg cuffs (64) may be attached to the remainder of the absorbent main body by bonding them to the topsheet at both longitudinal edges of the absorbent main body (38), such that at least in the crotch region (30), the leg cuffs are in active elasticity to provide gasketing around the leg openings.

The elastic belt (40) of the article of the present invention acts to dynamically create fitment forces and to distribute the forces dynamically generated during wear. The front and back elastic belts (84, 86) may be joined with each other only at the side edges (89) to form side seams (32), a waist opening and two leg openings. Each leg opening may be provided with elasticity around the perimeter of the leg opening. The elasticity around the leg opening may be provided by the combination of elasticity from the front elastic belt (84), the back elastic belt (86), and the leg cuffs (64).

The longitudinal length of the backsheet and the outer cover layer (42) may be the same, or may be varied. For example, the outer cover layer (42) may have a shorter length compared to that of the backsheet, such that the outer cover layer (42) is devoid where the absorbent main body (38) overlaps the elastic belt (40). By such configuration, the elastic belt may have better breathability. Further, such configuration may provide cost saving. The transverse width of the backsheet and the outer cover layer (42) may be the same, or may be varied. For example, the backsheet may have a shorter transverse width compared to that of the outer cover layer (42). By such configuration, the longitudinal side edges (48) of the crotch panel (56), which make part of the leg openings, may have better breathability. Further, such configuration may provide cost saving. The backsheet may extend to the transversely extending end edges (50) of the absorbent main body (38) for providing leakage prevention.

Figure 7:
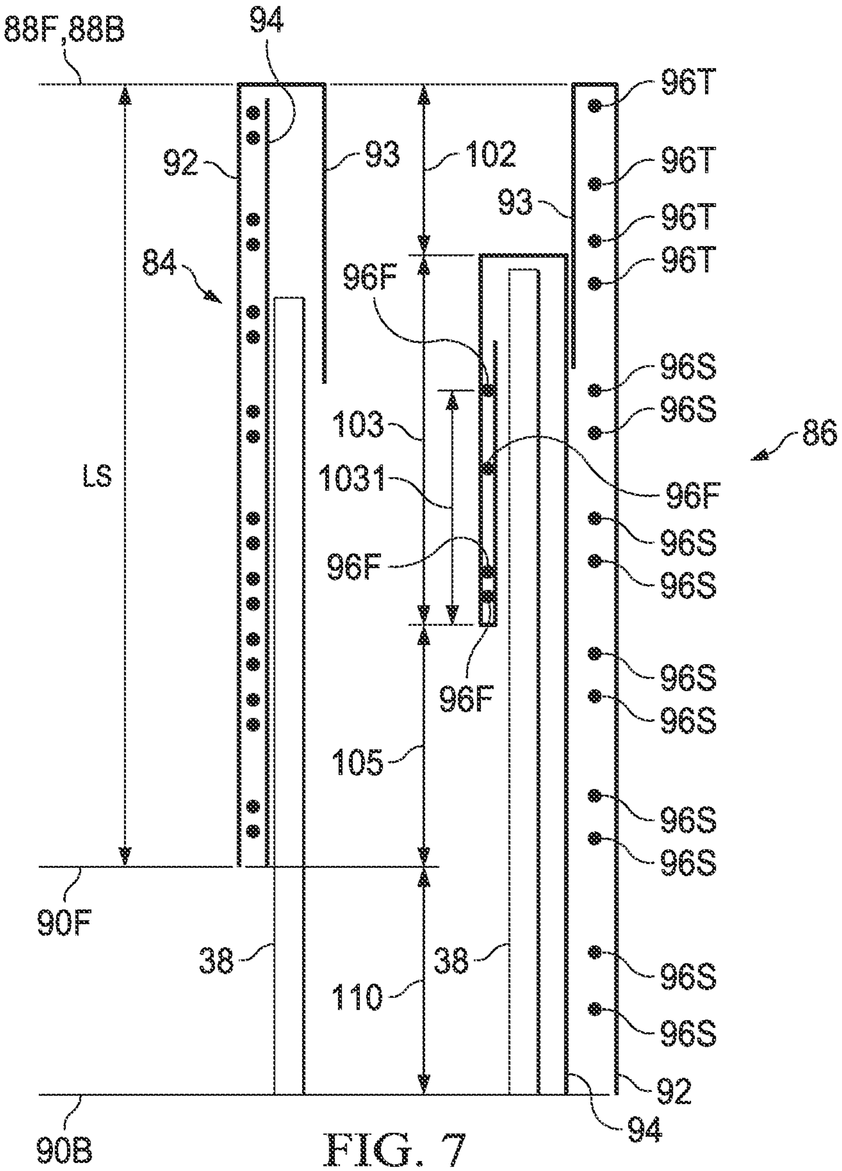
FIGS. 7 and 8 are schematic cross section views of front and back belt embodiments of FIGS. 2A-2B taken along line L2 and L3, with the thickness dimension exaggerated.

For the belt-type pant, the longitudinal length LB of the back elastic belt (86) and the longitudinal length LF of the front elastic belt (84) may be provided the same, or the back elastic belt (86) may have a greater longitudinal length LB as in FIG. 2A. Referring to FIGS. 2A and 7, when the wearable article is assembled to form the waist opening and the leg openings, the wearable article (20) may be folded along the transverse centerline T1 such that the front distal edge (88) is aligned with the back distal edge (88). The front side edge (89) is also aligned with a portion of the back side edge (89). Then the front elastic belt (84) and the back elastic belt (86) are joined at the front and back side edges (89) at the seams (32). The front and back proximal edges (90), however, may not be aligned to one another. The back proximal edge (90) may be disposed longitudinally closer than the front proximal edge (90) relative to the transverse center line T1 such that the proximal portion of the back side panel (82) extends toward the crotch panel (56) of the main body (38) beyond the front proximal edge (90). The side edge of the proximal portion of the back side panel (82) may not be joined to anywhere and free from attachment. Thus, the proximal portion of the back side panel (82) provides a buttock cover (not shown). Alternatively, referring to FIG. 8, for example when the waist guard portion (WGP) is disposed on the back elastic belt (86), the article (20) may be folded such that the front distal edge (88) exists more proximal than the back distal edge (88), as discussed in more detail below. In such configuration, the distal portion of the back elastic belt (86) extending beyond the front distal edge (88) may form a back waist extension (111). Such back waist extension (111) may communicate extra protection for back leakage.

The front elastic belt (84) and back elastic belt (86) are configured to impart elasticity to the belt (40). Referring to FIGS. 1, 2A, 7, and 8, the front elastic belt (84) and the back elastic belt (86) may each comprise a laminate, the laminate comprising a plurality of elastic members (96F, 96S) running in the transverse direction, an inner sheet (94), an outer sheet (92), an outer sheet fold over (93) wherein the outer sheet fold over is an extension of the outer sheet material formed by folding the outer sheet material at the distal edge (88) of the front and back elastic belts or otherwise; and one or a plurality of inner sheet fold overs (931, 932) wherein the inner sheet fold over is an extension of the inner sheet material formed by folding the inner sheet material at the distal edge (88) of the front and back elastic belts or otherwise; wherein the belt elastic members (96F, 96S) are sandwiched between two of these sheets. The front elastic belt (84) and the back elastic belt (86) may each be made only by elastic members (96S), the inner sheet (94), the outer sheet (92), and the inner and outer sheet fold overs (931, 932, 93). The belt elastic members (96F, 96S) may extend in the transverse direction to provide a ring like elastic belt (40) when the front elastic belt (84) and the back elastic belt (86) are joined. At least some of the elastic members (96F, 96S) extend in the transverse direction substantially parallel to each other. All of the elastic members (96F, 96S) may extend in the transverse direction substantially parallel to each other. Such an article may be economically made. The front and back elastic belt (84, 86) each may have transversely continuous proximal and distal edges, the proximal edge (90) being located closer than the distal edge (88) relative to the longitudinal center of the article. At least 10%, or at least from about 15% to not more than about 70%, of the front and back elastic belts from the waist opening in the longitudinal direction may be a laminate in active elasticity along the entire transverse dimension LW of the front and back elastic belts (84, 86). For each front and back elastic belt (84, 86), the region overlapping the front and/or back waist panel (52, 54) of the absorbent main body (38) may be removed of its elastic activity. Such region removed of elastic activity is referred herein as the "elastic cut window", and the remainder of the intact elastic member capable of imparting elasticity is defined as the "effective length of elasticity of an elastic member".

The tensile stress (N/m) of the entirety of the front and back elastic belts (84, 86), respectively, may be profiled in order to provide the functional benefits of the present invention, such as ease of stretch and application, while also maintaining certain force during wear, to prevent the article from sagging after loading. When the elasticity of the front and back elastic belts (84, 86) are provided by a plurality of elastic members (96F, 96S) running in the transverse direction, the tensile stress may be adjusted by one or more of the following methods; 1) elongation rate of the elastic member (96F, 96S); 2) density (dtex) of the elastic member (96F, 96S); 3) longitudinal pitch of multiple elastic members (96F, 96S); and 4) effective length of elasticity of the elastic member (96F, 96S) in the transverse direction. By elongation, "0% elongation" is meant the original length of the elastic member.

Figure 2B:
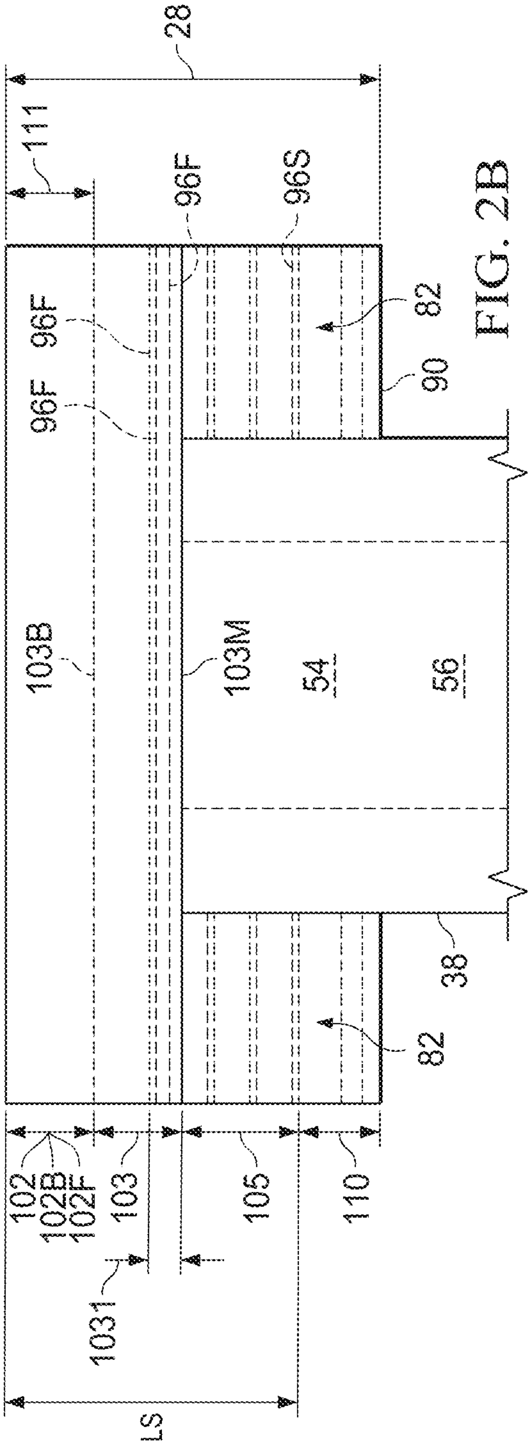
FIG. 2B-2C are schematic plan views of one belt embodiment of the present invention with the seams unjoined and in a flat uncontracted condition showing the body facing surface.

Referring to FIGS. 2A and 2B, the front and back elastic belts (84, 86) may each be divided into multiple zones spanning in the transverse direction and defined by its location from the distal edge (88) to the proximal edge (90) relative to the percentage of the seam length LS wherein the distal edge (88) is considered 0% and the proximal edge (90) is considered 100%. The multiple zones may be configured to provide different tensile stress, or different functions to the front and back elastic belts (84, 86), respectively. In the absorbent article of the present invention, a waist guard portion (WGP) may be disposed within a location of 5-70% of LS on one or both of the front and back elastic belts (84, 86), the waist guard portion (WGP) extending towards the crotch region from a closed base line (103B) toward an open edge (103M), wherein the waist guard portion (WGP) is partially bonded to the remainder of the front or back elastic belt (84, 86) to define a pocket (103P). FIG. 1 depicts a waist guard portion (WGP) on the back elastic belt. The waist guard portion (WGP) need not span the entire 5% to 70% of LS, but rather is comprised within such dimension.

The waist guard portion (WGP) may be positioned at a dimension of from about 25% to about 60% of LS, or from about 30% to about 65% of LS, or from about 25% to about 55% of LS, or from about 35% to about 70% of LS. Without being bound by theory, by providing the waist guard portion (WGP) in such dimension on the back elastic belt (86), the buttock cleavage of a wearer is effectively covered by the waist guard portion (WGP) so that low viscosity exudate, such as runny fecal matter or blood, may be effectively drawn into the pocket. Without being bound by theory, by providing the waist guard portion (WGP) in such dimension on the front elastic belt (84), the area matching the pubic bone of a wearer is effectively covered by the waist guard portion (WGP), so that low viscosity exudate, such as urine, may be effectively drawn into the pocket.

The waist guard portion (WGP) may be on the back elastic belt (86) and positioned at a dimension of from about 5% to about 50% of LS, or from about 10% to about 50% of LS. Without being bound by theory, by providing the waist guard portion (WGP) in such dimension on the back elastic belt (86), the back side is effectively covered towards the waist opening, so that fluid exudate such as urine, runny fecal matter or blood, may be effectively drawn into the pocket, even when the wearer is in active movement. The back elastic belt (86) may further have a back waist extension (111) as in FIG. 8. Without being bound by theory, by providing the waist guard portion (WGP) in such dimension on the back elastic belt (86) and further having the back waist extension (111), the back side is covered with these elements over a broad area, for example a greater area when the wearer is lying on ones back. Thus, fluid exudate such as urine, runny fecal matter or blood, may be effectively drawn into the pocket, and further protection is provided against back side leakage.

Referring to FIGS. 2B, 2C, and 3A-8, the waist guard portion (WGP) is explained by utilizing a number of embodiments provided on the back elastic belt (86). The waist guard portion (WGP) is made by an extension of the inner sheet (94), which extension of the inner sheet (94) is folded inwardly 2 times in order to encompass a first elastic member (96F) and further to provide the waist guard portion (WGP) in the intended position relative to the side seam length LS. As a result of the 2 folds, the first elastic member (96F) is sandwiched between the first inner sheet fold (931) and the second inner sheet fold (932), wherein the first inner sheet fold (931) constitutes the garment facing side of the waist guard portion (WGP), and the second inner sheet fold (932) constitutes the body facing surface. Referring to FIGS. 2C, 3D, 4D, 5D, and 6D, a certain longitudinal dimension from the distal edge of the second inner sheet fold (932) is bonded to the remainder of the belt, such bonding shown as SWFA, however, leaving some longitudinal dimension unbonded. The position provided most distal of the unbonded region is the closed base line (103B), and the common proximal edge of the first inner sheet fold (931) and second inner sheet fold (932) is the open edge (103M). The waist guard portion (WGP) is defined as having a longitudinal dimension spanning from the closed base line (103B) and the open edge (103M), and having a transverse dimension matching the width of the belt to which it is provided. The left and right transverse edges of the waist guard portion (WGP) are also bonded to the remainder of the belt, such bonding shown as SWFA. The unbonded region thus provided is the pocket (103P). The bondings provided to define the area of the pocket (103P) are so configured to provide the pocket (103P) substantially superposing the backsheet, preferably completely superposing the backsheet. Without being bound by theory, by providing the pocket (103P) substantially superposing the backsheet, this prevents low viscosity exudate having entered the pocket (103P) from flowing or penetrating out of the pocket (103P) towards the waist opening, or the transverse edges.

Figure 2C:
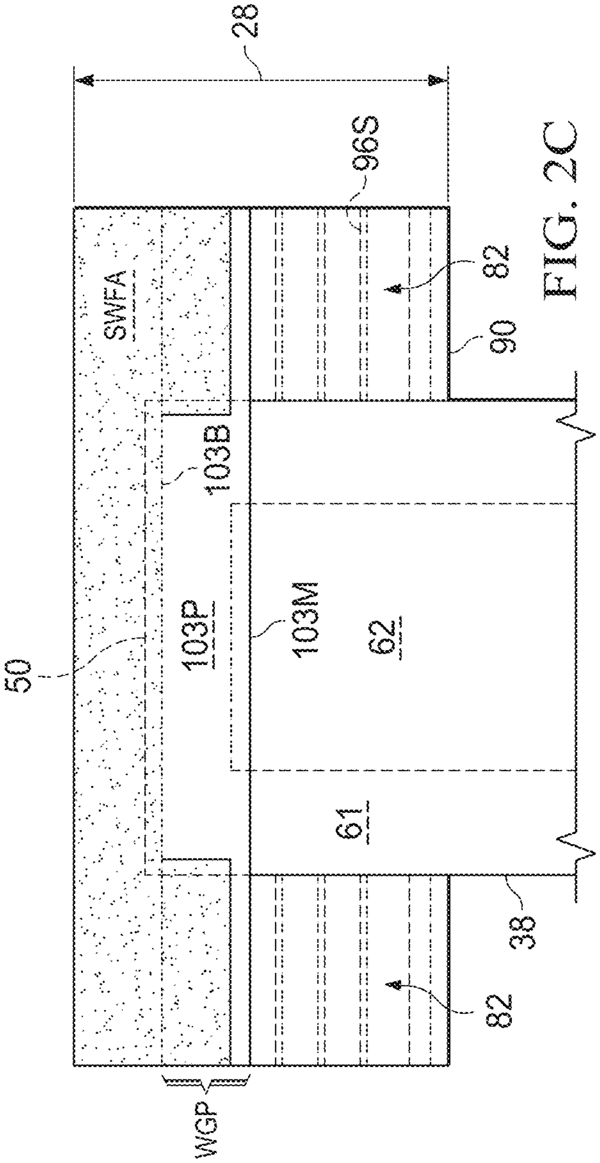

Referring to FIG. 2B, the first elastic member (96F) provides the waist guard elastic portion (WGEP), wherein elasticity may be imparted by one or more elastic strands, elastic ribbons, mechanically activated nonwovens, or otherwise. The waist guard elastic portion (WGEP) is defined as having a longitudinal dimension (1031) spanning from the open edge (103M) to the distal edge of the first elastic member (96F). When the first elastic member (96F) is a plurality of elastic strands, the distal edge of the waist guard elastic portion (WGEP) is the position of the elastic strand which is positioned most distal. There may be 2-10 elastic strands, or from 2-5 elastic strands, or 2-8 elastic strands, or 3-4 elastic strands, or 3-8 elastic strands, or 4-6 elastic strands disposed on the waist guard elastic portion. The longitudinal dimension of the waist guard elastic portion (WGEP) is smaller than that of the waist guard portion (WGP) such that a pocket (103P) having containment capacity may be provided. The longitudinal dimension of the waist guard elastic portion (WGEP) may be no greater than about 40 mm, or no greater than about 35 mm, or no greater than about 30 mm, or no greater than about 25 mm, or from 15 mm to about 40 mm, or from about 10 mm to about 35 mm, or from about 10 mm to about 25 mm. In FIGS. 2B and 2C, the pocket (103P) has a rectangular shape, however, the pocket (103P) may take other shapes by changing the bonding area SWFA such that the closed base line (103B) is shaped. For example, the closed base line (103P) may be concave or convex toward the pocket (103B) to match the wearer's anatomy. The longitudinal dimension of the pocket (103P) defined as the shortest distance between the closed base line (103B) to the open edge (103M) may be from about 20 mm to about 45 mm, or from about 24 mm to about 42 mm.

Referring to FIGS. 2C, 3D, 4D, 5D, and 6D, the remainder of the belt superposing the waist guard elastic portion (WGEP) is defined a correlated portion CP. Namely, the correlated portion CP has the same longitudinal dimension (1031) as the waist guard elastic portion (WGEP). The correlated portion CP may be elasticized or may not be elasticized, wherein the tensile stress of the waist guard elastic portion (WGEP) is higher than that of the correlated portion CP. The correlated portion CP may be elasticized wherein the tensile stress of the waist guard elastic portion (WGEP) is at least about 25% higher, or at least about 100% higher than that of the correlated portion CP. Without being bound by theory, such tensile stress difference enables the waist guard elastic portion (WGEP) to be in close contact with the wearer, while pulling away the open edge (103M) from the correlated portion CP, thus opening the pocket (103P) towards the proximal side. Thus, the pocket (103P) is configured to have good containment capacity. The correlated portion CP may have an elastic cut window such that some portion is elasticized, while the transverse center does not interfere with the opening of the pocket (103P). When the waist guard elastic portion (WGEP) is elasticized by disposing a plurality of elastic strands (96F), one elastic strand is disposed from no less than 2 mm to 5 mm away from the open edge (103M). Placement of the elastic strand on the very edge of the open edge (103M) may be avoided in order to prevent the waist guard portion (WGP) causing irritation to the wearer. The waist guard elastic portion (WGEP) may be disposed with a plurality of elastic strands (96F) with a relatively small pitch between each other. The elastic strands (96F) of the waist guard elastic portion (WGEP) may be disposed at a pitch of no more than about 12 mm, or no more than about 10 mm, or no more than about 6 mm, or between about 2 mm to about 8 mm, or between about 3 mm to about 9 mm, or between about 2 mm to about 6 mm.

The waist guard portion (WGP) may be configured in a certain way relative to the absorbent main body to provide improved function. As mentioned above, the area of the pocket (103P) are so configured to provide the pocket (103P) substantially superposing the backsheet, preferably completely superposing the backsheet. When the backsheet extends to the end edge (50) of the absorbent main body (38), the end edge of the backsheet matches the end edge (50) of the absorbent main body (38). Referring to FIGS. 2C, 3D, 4D, 5D, and 6D, the longitudinal edges of the absorbent main body (38) may be positioned and bonded between the waist guard portion (WGP) and the remainder of the belt. This is to avoid having sharp edges of the absorbent main body (38) on the body facing surface, and also to avoid leakage from the edges. The absorbent main body (38) comprises an absorbent material region (62) which may be surrounded by an absorbent material non-existing region (61), wherein the absorbent material region (62) having a greater thickness than that of the absorbent material non-existing region (61). The absorbent material region (62) may partially superpose the area of the pocket (103P) to provide at least some absorbent capacity in this region. At least about 3%, or at least about 10% of the area of the pocket (103P) may superpose the absorbent material region (62) toward the proximal edge. Even so, the combined thickness of the waist guard elastic portion (WGEP), the correlated portion CP, and the portion of the absorbent main body (38) sandwiched therebetween may be kept to no more than about 5 mm, preferably no more than about 4 mm. This is so that the thickness of the remainder of the article does not interfere with the opening of the pocket (103P) towards the proximal side due to the elasticity of the waist guard elastic portion (WGEP). When the absorbent main body (38) comprises an acquisition system, the acquisition system may be avoided from superposing the pocket (103P). In order to provide the waist guard portion (WGP) relative to the absorbent main body (38) in the aforementioned way, the distance between the waist opening to the longitudinal edge of the absorbent main body (38) may be adjusted, namely may be shifted toward the back side or the front side. For example, when the waist guard portion (WGP) is provided only on the back elastic belt (86), the distance between the waist opening to the longitudinal edge of the absorbent main body (38) may be made shorter on the back side than the front side.

The belt on which the waist guard portion (WGP) is disposed may be divided into 3 zones spanning in the transverse direction and defined by its location from the distal edge (88) to the proximal edge (90) relative to the percentage of the seam length LS wherein; 0% to the distal edge of the waist guard portion (WGP) is a waist zone (102), and the distal edge to the proximal edge of the waist guard portion (WGP) is a protective zone (103), and the proximal edge of the waist guard portion (WGP) to 100% is another zone. When there is an elastic member disposed at the distal edge or the proximal edge of the protective zone (103), such elastic member is considered to be included in the protective zone (103). Elastic members may be disposed on the remainder of the protective zone (103) which superposes the unelasticized area of the waist guard portion (WGP). Regardless of the existence of the waist guard portion (WGP), elastic members may be disposed on each of the waist zone (102), the protective zone (103) other than the waist guard portion (WGP), and another zone.

Referring to FIGS. 2A, 2B, and 7, when the waist guard portion (WGP) is disposed on the back elastic belt (86), the back elastic belt (86) may be divided into 3 zones spanning in the transverse direction and defined by its location from the distal edge (88) to the proximal edge (90) relative to the percentage of the seam length LS wherein; 0% to the distal edge of the waist guard portion (WGP) is a back waist zone (102B), the distal edge to the proximal edge of the waist guard portion (WGP) is a protective zone (103), and the proximal edge of the waist guard portion (WGP) to 100% is a buttock zone (105). The back elastic belt may further have a buttock cover zone (110), wherein the longitudinal dimension of the back elastic belt LB exceeds LS and the excess length is positioned on the proximal side of the front belt. Alternatively, referring to FIGS. 2A and 8, the back elastic belt may have a back waist extension zone (111) wherein the longitudinal dimension of the back elastic belt LB exceeds LS and the excess length is positioned on the distal side of the front belt. Elastic members may be disposed on each of the back waist extension zone (111), the protective zone (103) other than the waist guard portion (WGP), the buttock zone (105), and the buttock cover zone (110).

Referring to FIGS. 2A and 7, when the waist guard portion (WGP) is not disposed on the front elastic belt and the distal edges of the front belt (88F) and back belt (88B) are matched, the front elastic belt may be divided into 4 zones wherein: 0-25% is the waist zone (102) or front waist zone (102F), 25-50% is the distal tummy zone (104), 50-85% is the proximal tummy zone (106), and 85-100% is the leg zone (108). When there is an elastic member disposed at 25% from the distal edge (88), such elastic member is considered to be included in the waist zone (102). When there is an elastic member disposed at 50% from the distal edge (88), or 85% from the distal edge (88), such elastic member is considered to be included in the proximal tummy zone (106).

When the waist guard portion (WGP) is disposed on the back elastic belt and not disposed on the front elastic belt, the tensile stress of the protective zone (103) may be provided higher than the tensile stress of either the back waist zone (102B), or the buttock zone (105). When the waist guard portion (WGP) is disposed on the back elastic belt and not disposed on the front elastic belt, the tensile stress of the front proximal tummy zone (106) may be provided higher than the tensile stress of any of the front waist zone (102F), the front distal tummy zone (104), or the front leg zone (108). The tensile stress of the front proximal tummy zone (106) may be higher than the tensile stress of any other zone, either in the front or the back. When comparing all of the zones of the front elastic belt and the back elastic belt, the tensile stress may be provided greatest in the order of: the front proximal tummy zone (106), followed by the protective zone (103). Without being bound by theory, such profiling of the tensile stress per zone is believed to provide the article of the present invention with a shaped elastic belt (40) that conforms well to a human body, particularly to a lower torso of a child of less than 36 months of age, and therefore provide good fit and comfort to the wearer, without compromise of sagging prevention or leakage prevention. Namely, the front proximal tummy zone (106) is subject to high tensile stress such that the article may be anchored against the wearer's trochanter, while leaving more area for the buttock zone (105) to accommodate the wearer's buttock.

Referring to FIGS. 3A-8, the elastic belts of the present invention may be made by a relatively simple structure comprising no more than the inner sheet (94), the outer sheet (92), the first inner sheet fold (931), the second inner sheet fold (932), the optional outer sheet fold (93), and the first and second elastic members (96F, 96S) encompassed within these layers. The inner sheet (94) may be a hydrophobic nonwoven layer of relatively low basis weight, such that the waist guard portion (WGP) is kept as thin as possible, while providing leakage prevention. The outer sheet (92) may be a nonwoven layer, and wherein the basis weight of the outer sheet (92) is greater than that of the inner sheet (94). The outer sheet (92) may be a lofty and soft nonwoven of relatively higher basis weight to connote high quality. Any portion of the elastic belt comprising the waist guard portion (WGP) may be made by less than 6 layers, or made by 3-4 layers, and in a thickness of no more than about 5 mm, or no more than about 4 mm. Providing the belt structure simple and relatively thin is advantageous in maintaining breathability and softness of the belt.

The elastic belts of the present invention may be made by elastic strands commonly used in the art having a density of no more than 940 dtex. Certain zones of the belt may be disposed of elastic members having a density of no more than about 500 dtex, thus providing a soft fit. Elastic members having a density of no more than about 500 dtex may be disposed on one or more of the waist zone (102) or the front leg zone (108). Without being bound by theory, it is believed that elastic members of relatively low density impart an easy initial stretch experience when stretch opening the article (20), while maintaining a good fit during wear. The article of the present invention may be provided with a protective measure for preventing leakage of low viscosity bodily exudates from the waist opening, while maintaining good stretchability for ease of application, good fit for preventing sagging, good comfort and softness, and good breathability. The present article may have a Waist Circumference Force according to the Whole Article Force Measurement herein of no more than about 9N, or no more than about 8N.

In the present invention, at least one of the inner sheet (94), the outer sheet (92), or the outer cover layer (42) may further comprise a plurality of apertures, wherein the individual aperture may be in the shape of an oval, or polyhedron, while having an aspect ratio of no more than about 3, or no more than about 2.5. The individual aperture may have a transverse dimension APT of at least about 0.4 mm, or from about 0.4 mm to about 2.0 mm, and a longitudinal dimension APL, wherein APT is at least about 10% greater than APL. Further, the individual apertures may be spaced apart from each other with a longitudinal pitch DF2 of no more than about 5 mm, and APL is not larger than 50% of DF2, or APL is from about 12% to about 30% of DF2. Apertures of such size, shape, and spacing may be visible to the naked eye on the garment-facing surface. When apertures are provided on the outer sheet (92), this may connote breathability and high quality of the gathers made by the contraction of the elastic members of the elastic belt (40), even when the gathers are in contracted state. By providing apertures on the outer sheet (92) and not on the inner sheet (94), this may connote breathability while preventing the perception that the waist guard portion (WGP) may cause leakage from the apertures. By providing apertures on the outer sheet (92) and the outer cover layer (42) and further coordinating the patterns of apertures, this may enhance integral appearance of the elastic belt (40) and absorbent main body (38).

Referring to FIGS. 1, 2A, and 3D, 4D, 5D, and 6D, even when the back elastic belt (86) comprises a waist guard portion (WGP), the remainder of the back elastic belt (86), and particularly the garment facing surface of the back elastic belt (86), may be maintained in a simple structure. This enables the article to have other functions that are desired of a pant type absorbent article, such as having a disposal tape attached to the garment facing surface of the back elastic belt (86). Accordingly, the absorbent article may be devoid of fastening means.

Referring to FIGS. 3A-8, the steps for making various variations of the absorbent article of the present invention is explained, utilizing embodiments wherein the back elastic belt (86) comprises the waist guard portion (WGP). While only the back belt is shown in FIGS. 3A-6F, the waist guard portion (WGP) may be made in the same way on the front elastic belt (84). Further, the front and back elastic belts may be formed from the same continuous first and second sheets (94C, 92C). The elastic belts of the present invention may be made by a process comprising the steps of providing 2 folds for the inner sheet (94) and keeping the elastic belt (40) soft and relatively thin. The process comprises introducing elastic strands (96F) for the waist guard elastic portion (WGEP) by the first fold (931), configuring the waist guard portion (WGP) by the second fold (932), and configuring a pocket (103P) by bonding certain portions of the first and second fold (931, 932) to the remainder of the back elastic belt (84) or the back waist panel (54, 38). The main differences compared to methods for making articles devoid of the waist guard portion (WGP) include; providing the inner sheet (94) in longer longitudinal dimension of the article, or wider dimension in the CD direction, and having an additional step of providing 2 folds of the inner sheet (94), rather than 1 fold. An additional step of providing a fold of the outer sheet (92) may be included. Such differences may be effected conveniently by changing the upstream of currently available methods for making a pant-type article. This enables change over of making the absorbent article of the present invention from those devoid of the waist guard portion (WGP) relatively easy. The manufacturing method of the present invention is described in further detail below.

Figure 9:
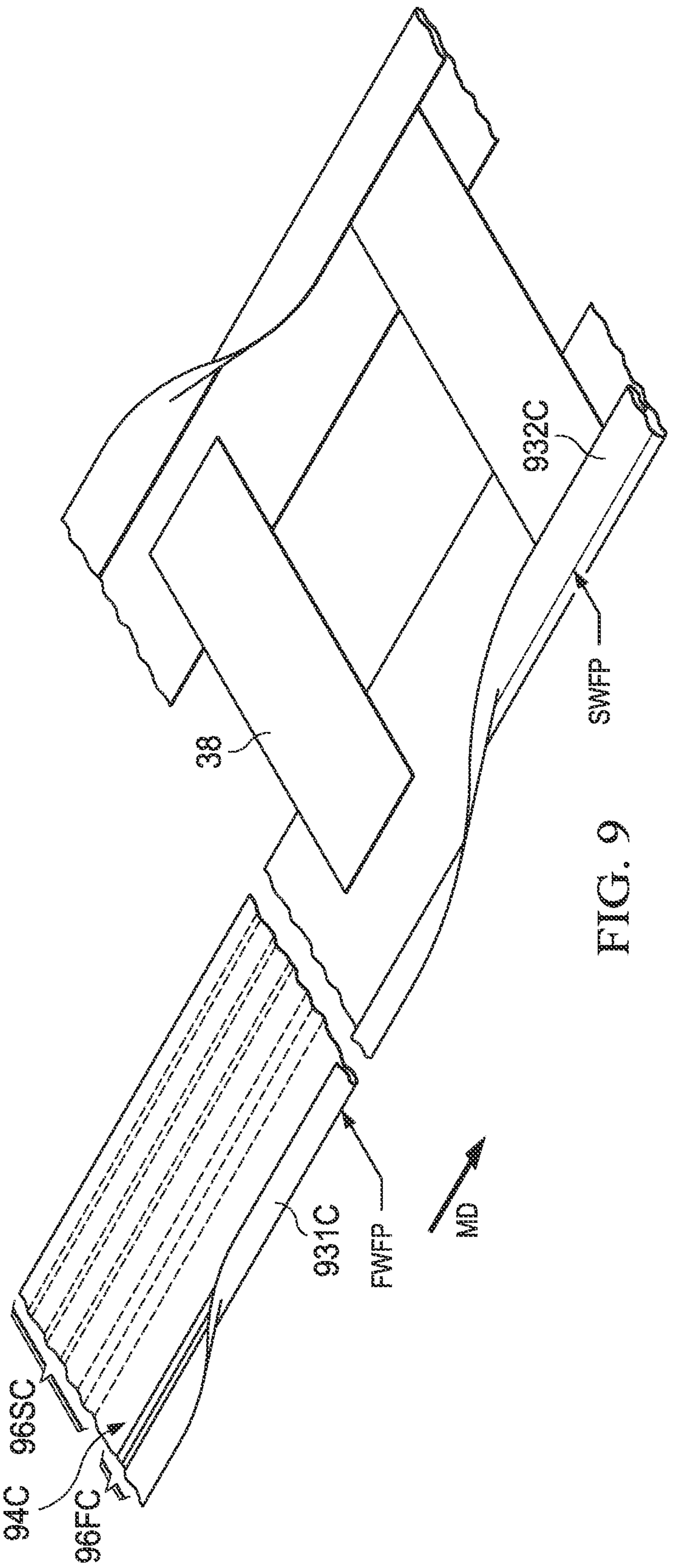
FIG. 9 is a schematic view of the folding steps of the present invention.

Referring to FIG. 9, the present method is directed to providing a waist guard portion (WGP) to at least one of the front elastic belt (84) or the back elastic belt (86) by minor additions and modifications to currently available methods for making a pant-type absorbent article. FIG. 9 specifically describes a method for making a belt-type pant. Namely, referring to FIGS. 9 and 3A-6D, an additional first folding step is added to the upper flow of the process. The first folding step as in FIGS. 3A-3B, 4A-4B, 5A-5B, and 6A-6B, introduces the first elastic strands (96F), and a second folding step as in FIGS. 3C-3D, 4C-4D, 5C-5D, and 6C-6D configures the waist guard portion (WGP). The method enables using the same number of elastic strands for the belt, compared to products devoid of the waist guard portion (WGP), while also enabling manufacture at a similar line speed. The line speed may be at least about 200 meters per minute, or at least about 250 meters per minute, or at least about 300 meters per minute, or at least about 350 meters per minute, or at least about 400 meters per minute.

In the finished article, the first layer of continuous sheet (94C) becomes the inner sheet (94), the second layer of continuous sheet (92C) becomes the outer sheet (92), the first elastic members (96FC) become the elastic members (96F) for the waist guard elastic portion (WGEP), the second elastic members (96SC) become the elastic members (96S) disposed between the inner and outer sheets (92, 94), and the pocket (103P) is formed by the unbonded portions of the first and second folds (931C, 932C). Referring to FIGS. 6A-6B, 7, and 8, there may additionally be a third elastic member (96T) introduced within the outer sheet (92) and outer sheet fold over (93).

The present method comprises the following 4 steps.

A) Forming the Waist Guard Precursor

Referring to FIGS. 3A-3B, 4A-4B, 5A-5B, and 6A-6B, and 9, this step comprises advancing a first layer of continuous sheet (94C) having an inner surface and an opposing outer surface in a machine (MD) direction and having a first width in a cross machine (CD) direction; advancing a plurality of first elastic members (96FC) in the machine direction in a stretched state; bonding the first elastic members (96FC) on the inner surface of the first layer (94C); folding the width edge of the first layer (94C) along the machine direction at a first waist fold point (FWFP) to form a first inner waist fold (931C); and bonding the first elastic members (96FC) between the inner surface of the first layer (94C) and the first inner waist fold to form (931C) a first layer assembly (FLA) comprising a waist guard precursor (WGPP), the waist guard precursor (WGPP) defined as the first inner waist fold (931C), the first elastic members (96FC), and the first layer facing the first inner waist fold.

The first inner waist fold (931C) is made by folding the first layer at the first waist fold point FWFP. The first elastic members (96FC) may be secured within the waist guard precursor (WGPP) by a first waist fold adhesive FWFA provided on the first continuous sheet (94C). The continuous first elastic members (96FC) may also be applied adhesive (228) prior to bonding to the first continuous sheet (94C). The first elastic members (96FC) may be bonded to either or both layers of the first continuous sheet (94C) by adhesive continuously, or intermittently. When the first elastic members (96FC) are bonded intermittently, the bonding pattern may be so arranged that the bonding only exists along the side seams per article.

B) Forming the Remainder of the Elastic Belt

Referring to FIGS. 3B, 4B, 5B, and 6B, and 9, this step comprises: advancing a second layer of continuous sheet (92C) having an inner surface and an opposing outer surface in the machine direction and a second width in the cross machine (CD) direction; advancing a plurality of second elastic members (96SC) in the machine direction in a stretched state; bonding the second elastic members (96SC) to the inner surface of the second layer (92C) to form a second layer; and bonding the inner surface of the second layer to the outer surface of the first layer assembly (FLA).

While not illustrated, the continuous second elastic members (96SC) may also be applied adhesive (228) prior to bonding between the first and second continuous sheets (92C, 94C). The second elastic members (96SC) may be bonded to either or both layers of the first continuous sheet (94C) continuously, or intermittently. When the second elastic members (96SC) are bonded intermittently, the bonding pattern may be so arranged that the bonding only exists along the side seams per article. There may be provided vertical adhesive to the first and/or second continuous sheets (92C, 94C) in continuous or discontinuous lines in the CD direction and spaced apart in the MD direction. Such vertical adhesive may be utilized for intermittently bonding the first and second elastic members (96FC, 96SC).

Figures 4A, 4B, 4C, 4D:
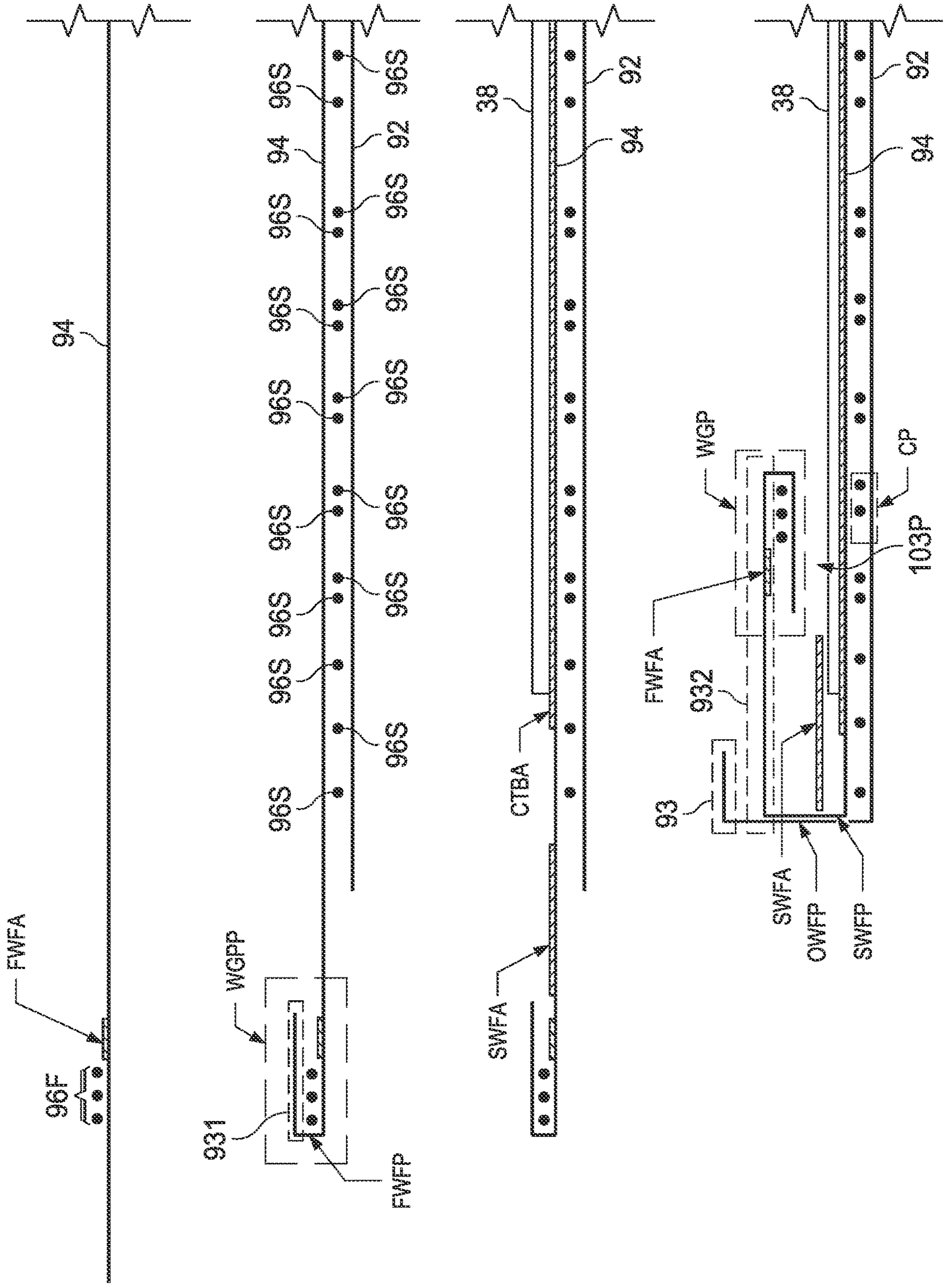
FIGS. 4A-4D are schematic cross section views of precursors for making another embodiment of FIGS. 2A-2C taken along line L2, with the thickness dimension exaggerated.
Figures 5A, 5B, 5C, 5D:
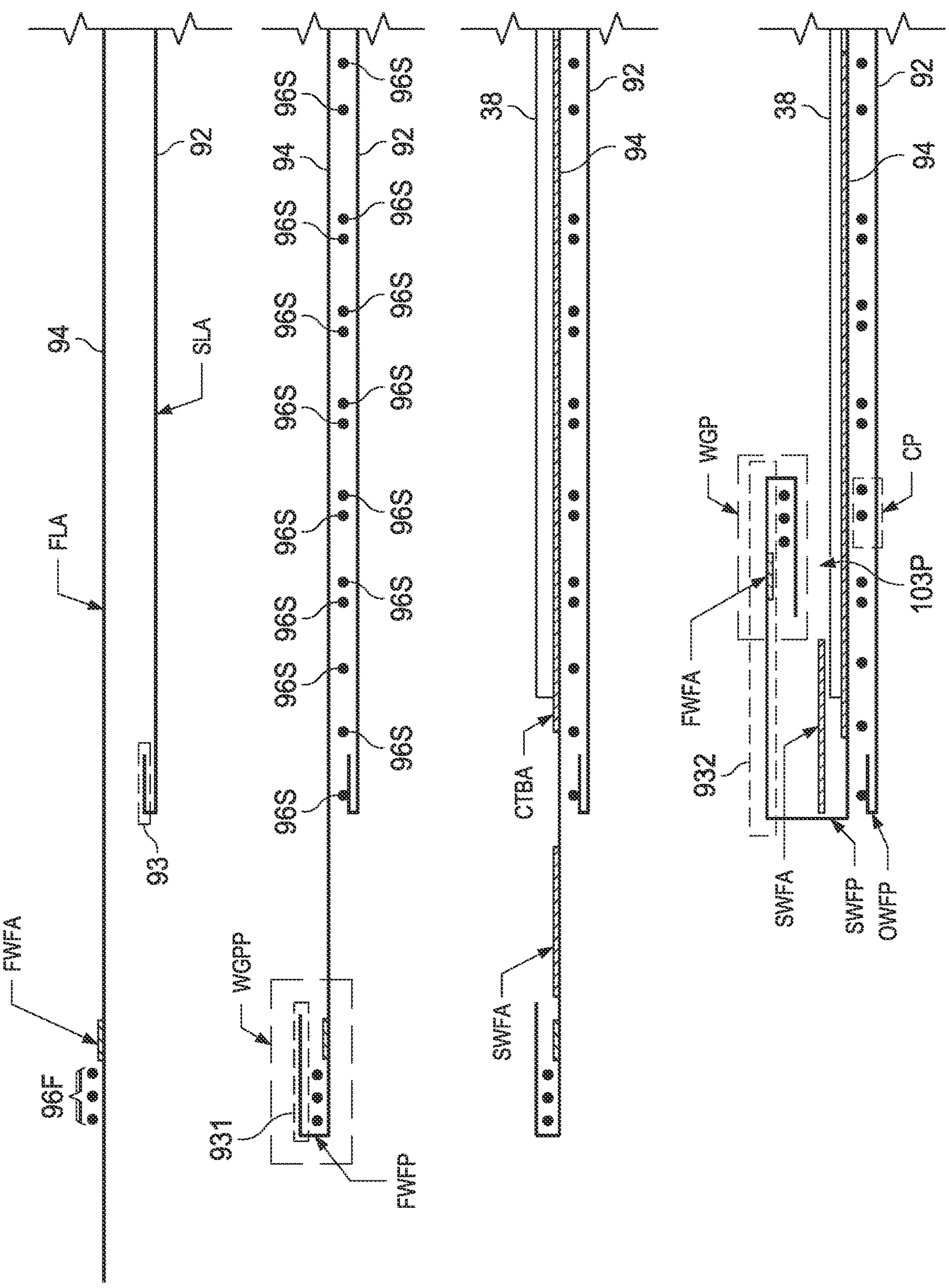
FIGS. 5A-5D are schematic cross section views of precursors for making another embodiment of FIGS. 2A-2C taken along line L2, with the thickness dimension exaggerated.

Referring to FIG. 5B, prior to the step of introducing the second elastic members (96S) and bonding the inner surface of the second layer (92) to the outer surface of the first layer assembly (FLA), there may be a step of folding the width edge of the second layer (92) along the machine direction at an outer waist folding point (OWFP) to form an outer waist fold (93) attached to the inner surface of the second layer. The second layer (92) having the outer waist fold (93) thus formed may be referred as the second layer assembly (SLA). Referring to FIG. 5D, by providing such outer waist fold (93), this may avoid having the edge of the outer sheet (92) adjacent the waist opening, and further keep the waist opening relatively thin compared to, for example FIG. 4D.

Figure 6A:
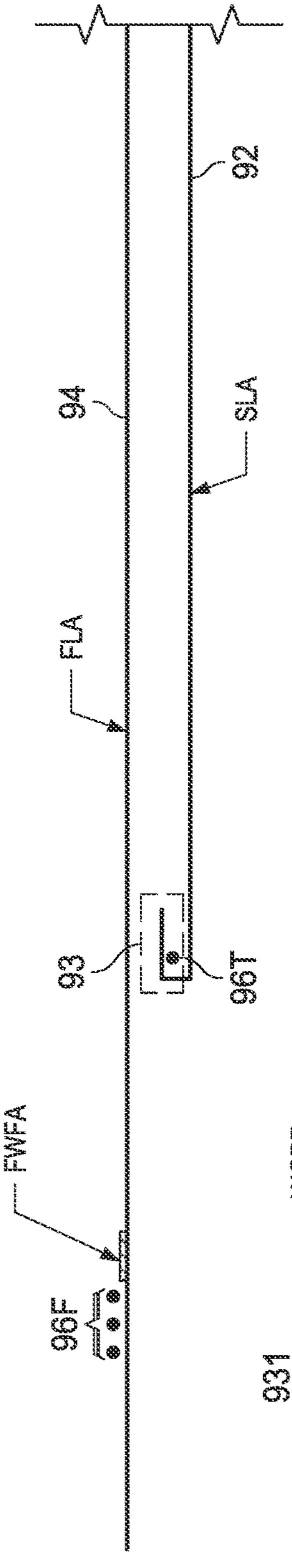
FIGS. 6A-6D are schematic cross section views of precursors for making another embodiment of FIGS. 2A-2C taken along line L2, with the thickness dimension exaggerated.
Figure 6B:
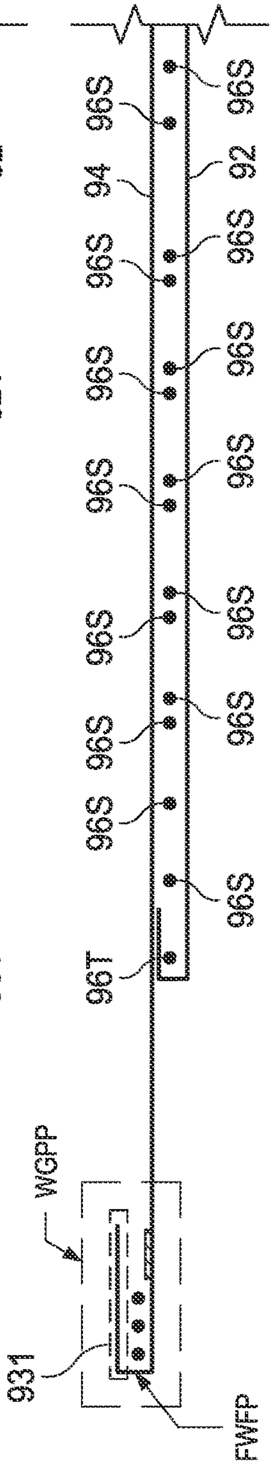
Figure 6C:
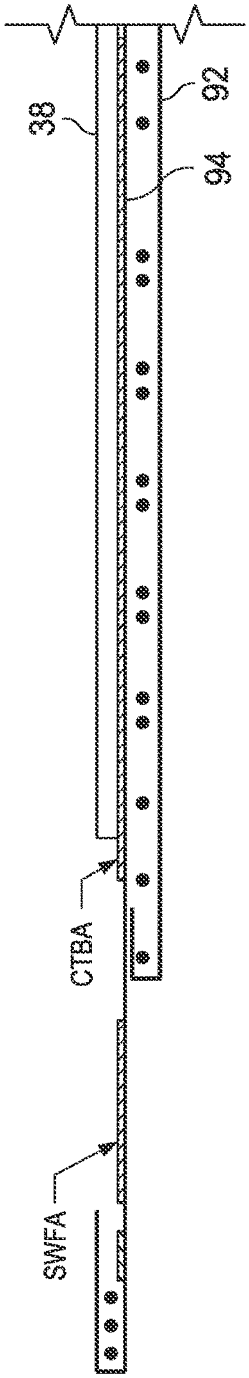
Figure 6D:
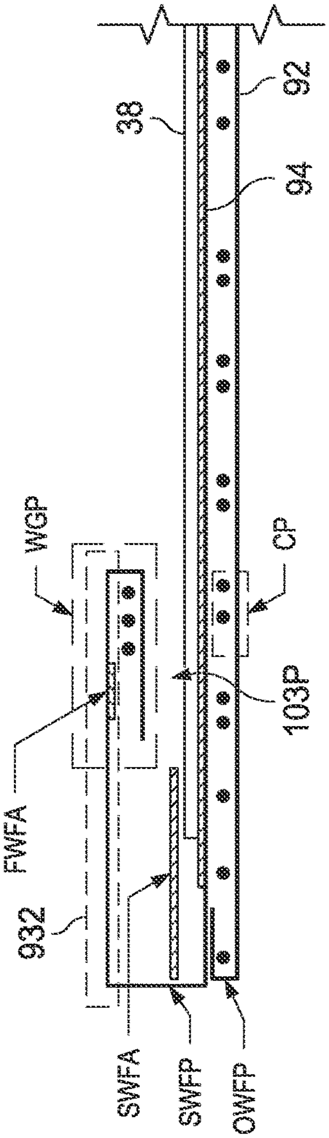

Referring to FIG. 6B, prior to the step of introducing the second elastic members (96S) and bonding the inner surface of the second layer (92) to the outer surface of the first layer assembly (FLA), there may be a step of advancing a third elastic member (96T) in the machine direction in a stretched state; folding the width edge of the second layer (92) along the machine direction at an outer waist folding point (OWFP) to form an outer waist fold (93) attached to the inner surface of the second layer (92) and to sandwich the at least one third elastic member (96T). The assembly formed by the second layer (92), the outer waist fold (93) and third elastic member (96T) sandwiched therebetween may be referred as the second layer assembly (SLA). Referring to FIG. 6D, by providing such outer waist fold (93), this may provide a favorable finished appearance to the waist opening. The third elastic member (96T) may be a single elastic member, or plurality of elastic strands.

Figure 8:
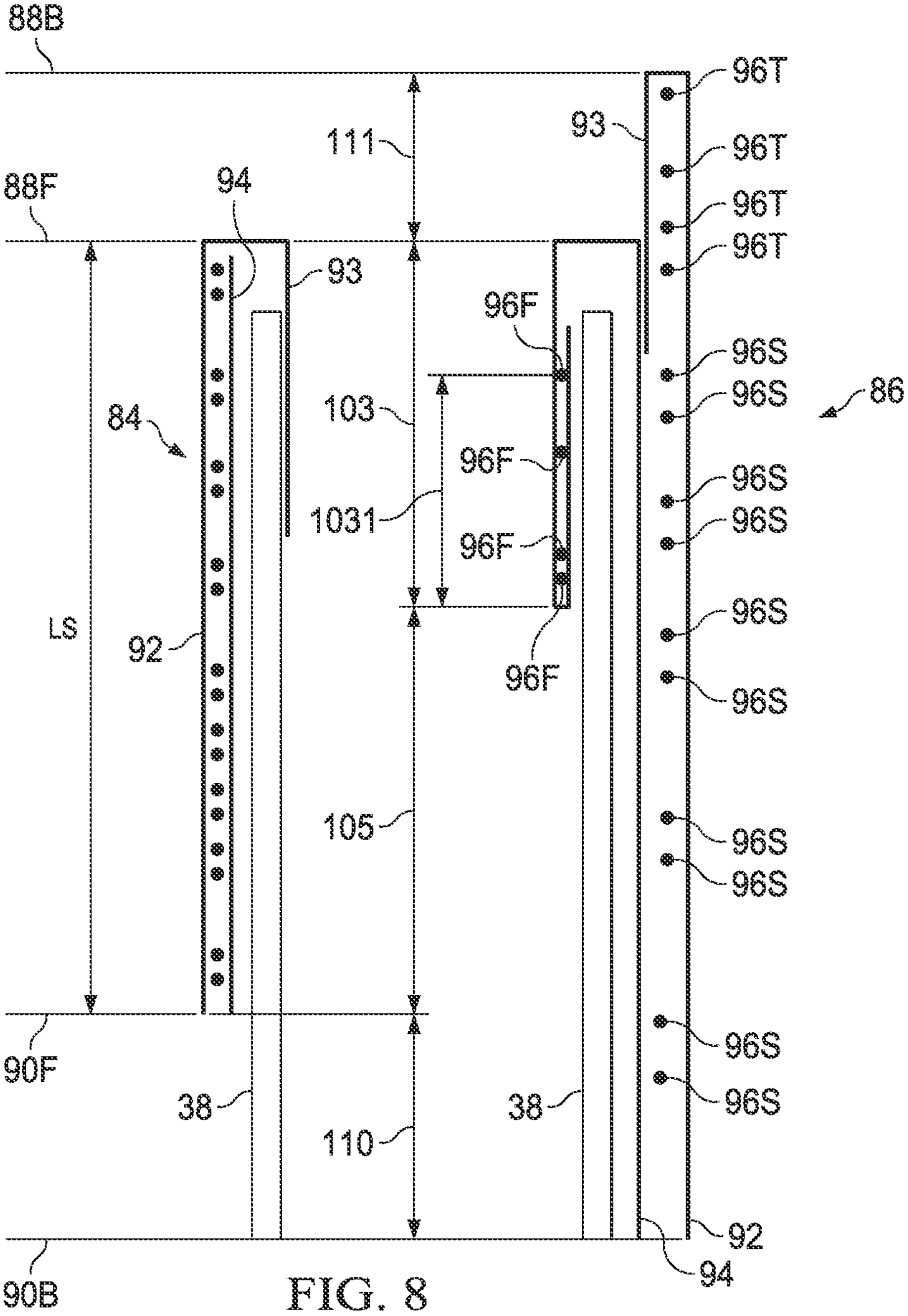

Referring to FIGS. 7 and 8, the second width of the second layer (92C) may be provided as such that it enables the proximal edge of the outer waist fold (93) to extend further proximal than the second inner waist fold (SWFA). By such configuration, this enables positioning the second inner waist fold point (SWFP) to be closer to the distal edge (50) of the absorbent main body (38) while avoiding any second elastic members (96S) being exposed. This may provide material savings for the first layer (94), and provide the region adjacent the waist opening with fewer layers of material and hence thin and breathable. Still further, this configuration enables assembling with the front elastic belt (84) as in FIG. 8, to provide a waist extension (111).

Step B) may follow immediately after Step A) in order to reduce exposure time of any adhesives utilized during the steps. The forming of the second layer assembly (SLA) may be conducted simultaneously with, or prior to Step A). Following Step A) and forming of the second layer assembly (SLA), the reminder of Step B) may be effected substantially simultaneously, also to reduce exposure time of any adhesives utilized during the steps. Further, depending on whether or not elastic cut windows are desired for the second elastic members (96SC), the second elastic members (96SC) may be grouped prior to joining with the first and second continuous sheets (92C, 94C). As explained above, certain of the second elastic members (96SC) may have an elastic cut window to remove elastic activity over a certain length in the region overlapping the front and/or back waist panel (52, 54). Such elastic cut window may be made by leaving the elastic member unbonded to the first or second continuous sheets (92C, 94C) and severing the elastic member. When the bonding is provided by applying adhesive, it may be convenient to group the elastic members into those which have an elastic cut window and those which do not. Those elastic members which do not have an elastic cut window may be applied adhesive over the entire length per article of the elastic members, while those elastic members that have an elastic cut window may be applied adhesive intermittently. Referring to FIGS. 3A-3B and 4A-4B, when there is no second layer assembly (SLA) forming, the first elastic members (96FC) and elastic members to be eventually continuously bonded along the waist opening (96SC) may be introduced in one group with continuous adhesive application, while the remainder elastic members to have an elastic cut window (96SC) may be introduced in another group with intermittent adhesive application. Steps A) and B) may be effected substantially simultaneously for making both the front and back elastic belts (84, 86).

C) Attaching the Absorbent Main Body

Referring to FIGS. 3C, 4C, 5C, 6C, and 9, this step comprises bonding the absorbent main body (38) to the inner surface of the first layer (94C). Chassis to belt adhesive (CTBA) may be applied to the outer surface of the second layer (94C) for this bonding. While not illustrated, the chassis to belt adhesive (CTBA) may be provided in stripes continuous in the MD direction and spaced apart in the CD direction.

Preceding Step C), when the absorbent article is a belt-type pant, the jointly created front and back elastic belt assembly may be separated by a slit cutter while the absorbent main body (38) may be formed by cutting a continuous absorbent main body into discrete pieces, and processing through a transferring apparatus to turn the absorbent main body (38) by a certain angle while spacing the absorbent main body (38) as appropriate, and transferred to be joined such that the transverse axis of the absorbent main body (38) is aligned with the MD direction of the elastic belt making assembly.

D) Forming a Waist Guard Portion

Referring to FIGS. 3D, 4D, 5D, 6D, and 9, this step comprises;

folding the assembly thus obtained along the machine direction at a second inner waist folding point (SWFP) between the waist guard precursor (WGPP) and the absorbent main body (38) to form a second inner waist fold (932) wherein a portion of the absorbent main body (38) is sandwiched between the proximal edge of the second inner waist fold (932) and the inner surface of the first layer (94C); and bonding a certain portion of the first inner waist fold and a certain portion of the second inner waist fold to the remainder of the belt assembly to which it faces, wherein the unbonded outer surfaces of the first inner waist fold (931) and the second inner waist fold (932) form a pocket (103P). For this bonding, a second waist fold adhesive (SWFA) may be applied to the first inner waist fold (931) as well as the inner surface of the first continuous sheet (94C) which is planned to become the second inner waist fold (932). Referring to FIG. 2C, the second waist fold adhesive SWFA is so applied that there is an opening in the transverse center of the obtained article. The second waist fold adhesive SWFA may be applied so that the obtained article is bonded over the entire dotted area, or may be provided in stripes or spirals, or other shapes which cover the dotted area in enough bonding to bear any detachment during usage, and to avoid contained exudate penetrating outside the pocket.

Figures 3A, 3B, 3C, 3D:
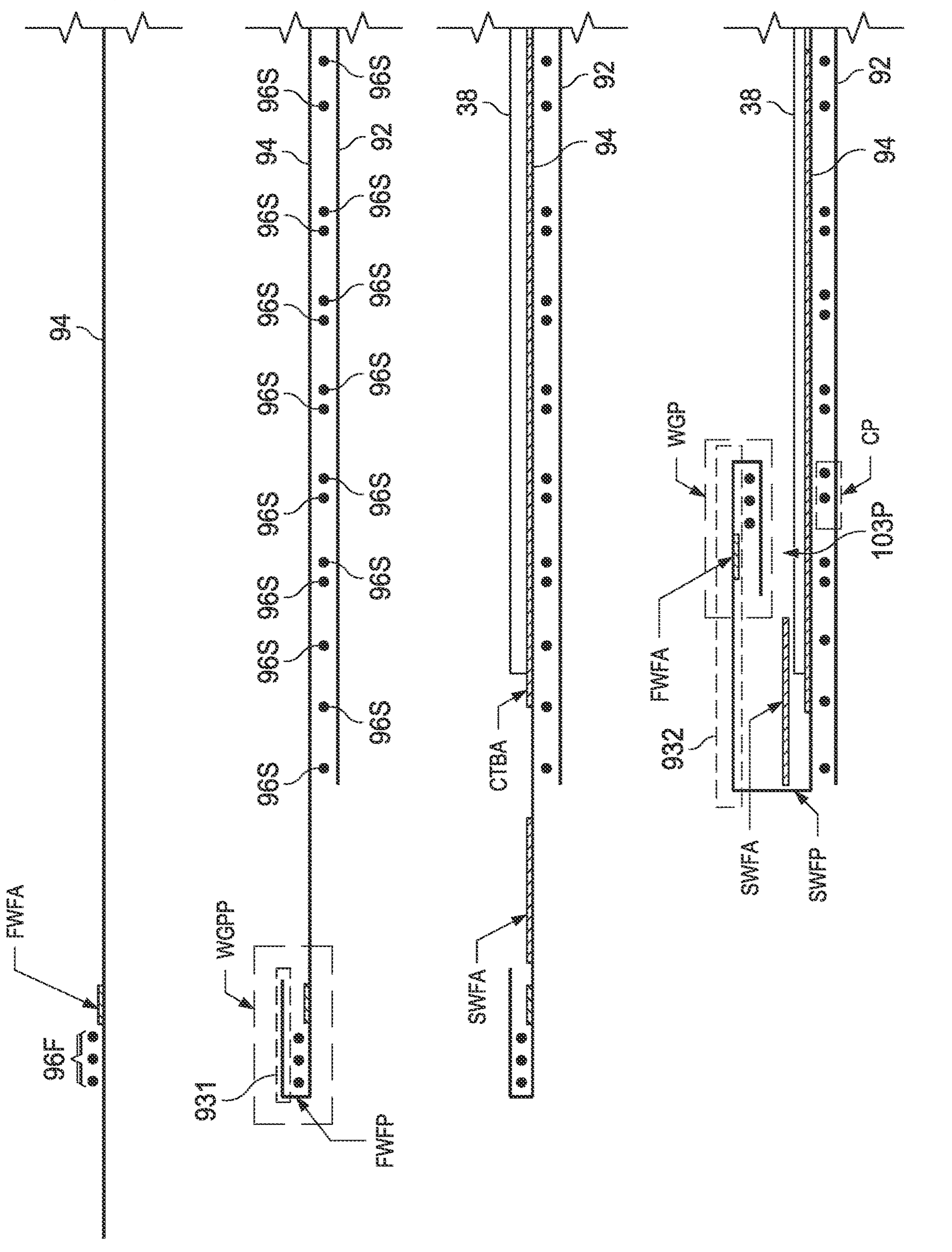
FIGS. 3A-3D are schematic cross section views of precursors for making an embodiment of FIGS. 2A-2C taken along line L2, with the thickness dimension exaggerated.

Referring to FIGS. 3B-3D, upon folding the assembly for making the second inner waist folding point (SWFP), the second inner waist folding point (SWFP) may be positioned between the waist guard precursor (WGP) and the second width edge of the second layer (92C). Referring to FIG. 3D, by providing the second width of the second layer (92C) as such, the second inner waist folding point (SWFP) becomes the resulting waist opening, and the distal edge of the outer sheet (92) is kept away from the waist opening, while securing the second elastic members (96S) within the elastic belt.

Referring to FIGS. 4B-4D, there may be an additional step of concurrently folding the waist guard precursor (WGP) and the second layer (92C) along the machine direction at the second inner waist folding point (SWFP) to form the second inner waist fold (932), an outer waist folding point (OWFP) and an outer waist fold (93), wherein the second width of the second layer (92C) is such that it enables a certain width of the outer waist fold (93) existing on the wearer facing side of the second inner waist fold (932). Referring to FIG. 4D, by providing such outer waist fold (93), there are many layers at the waist opening, providing a cushiony feel at the waist opening. Further, this may avoid having the edge of the outer sheet (92) adjacent the waist opening.

Steps C) and D) may be effected substantially simultaneously in order to reduce exposure time of any adhesives utilized during the steps.

The obtained assembly after Step D) is then folded at a certain point in the CD direction to obtain a final continuous assembly. The final continuous assembly is then seamed at the planned left and right edges of the article, and then finally cut to obtain individual absorbent articles. Referring to FIG. 7, the folding may be provided along the transverse centerline T1 such that the front distal edge (88) is aligned with the back distal edge (88), wherein the front and back proximal edges (90) may not necessarily be aligned to one another. Referring to FIG. 8, when the waist guard portion (WGP) is provided on the back belt (86) but not on the front belt (84), the folding may be provided such that the front distal edge (88) exists more proximal than the back distal edge (88), for example, the front distal edge (88) may match the second inner waist folding point (SWFP) of the back belt (86). The distal portion of the back elastic belt (86) extending beyond the front distal edge (88) may form a back waist extension (111).

EXAMPLES

Examples A-E

Belt-type pant absorbent article of the present invention in Size 3 (M size) having an elastic profiling of the back elastic belt and other configurations/dimensions according to Table 1 below. For each example, the distal edge of the front elastic belt is aligned with the distal edge of the back elastic belt. For each example, the protective zone comprising the waist guard portion (WGP) is positioned at a location within 25-60% of LS only on the back elastic belt. For each example, the waist guard elastic portion (WGEP) has a higher tensile stress than the correlated portion CP.

TABLE 1

| Example | A | B | C | D | E |
|---|---|---|---|---|---|
| Configuration (Fig) | 3D | 4D | 5D | 6D | 7 |
| | dtex/elongation %/number of elastic members (dimension of elastic cut window) | | | | |
| Waist zone | 470 dtex/180%/3 | | | | |
| Protective zone Waist Guard Portion | 940 dtex/210%/4 | | | | |
| Protective zone other than Waist Guard Portion | 470 dtex/180%/1<br>940 dtex/130%/2 (114 mm) | | | | |
| Buttock zone | 940 dtex/130%/2 (114 mm)<br>470 dtex/240%/3 (114 mm) | | | | |
| Buttock cover zone | 470 dtex/240%/3 (114 mm) | | | | |

Examples A-E provide good stretchability for ease of application, good fit for preventing sagging, good comfort and softness, good breathability at the waist opening, good protection against leakage of runny fecal matter from the waist opening on the back side, and ease of tearing upon disposal, Examples B, C, and D provide a cushiony feel at the waist opening. Example E provides a finished appearance.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An absorbent article having a longitudinal direction and a transverse direction comprising a front elastic belt, a back elastic belt, a crotch region, a waist opening, and a pair of leg openings; the crotch region extending longitudinally between the front elastic belt and the back elastic belt; each of the front and back elastic belt is formed by an outer sheet, an inner sheet, and a second elastic member bonded directly to the outer sheet and the inner sheet, wherein the outer sheet is the garment-facing surface;

the absorbent article comprising an absorbent main body extending the entire longitudinal dimension of the crotch region and further extending partly into each of the front elastic belt and the back elastic belt, the absorbent main body comprising a liquid pervious topsheet, a liquid impervious backsheet, and an absorbent material region sandwiched therebetween;

wherein the inner sheet of the back elastic belt comprises a first inner waist fold and a second inner waist fold forming a waist guard portion extending towards the crotch region from a closed base line towards an open edge, wherein the first inner waist fold extends outward from a first waist fold point to a distal edge, and the second inner waist fold extends between the first waist fold point and a second waist fold point, the first waist fold point positioned inward from the second waist fold point, and wherein the first inner waist fold is sandwiched between the second inner waist fold and a non-folded region of the inner sheet, and a first elastic member bonded between the first inner waist fold and the second inner waist fold, wherein the waist guard portion is partially bonded to the remainder of the back elastic belt from which the first and second inner waist folds extend, to define a pocket; and wherein the outer sheet of the back elastic belt extends to form an outer waist fold, wherein the outer waist fold is sandwiched between the outer sheet and the inner sheet.

2. The absorbent article of claim 1, wherein a third elastic member is sandwiched between the inner sheet and the outer waist fold.

3. The absorbent article of claim 1, wherein a third elastic member is sandwiched between the outer sheet and the outer waist fold.

4. The absorbent article of claim 3, comprising a second inner waist folding point formed at the fold point between the first and second inner waist fold, wherein the second inner waist fold point is positioned proximal than to the waist opening.

5. The absorbent article of claim 4, wherein the waist guard portion is provided on the back elastic belt and not on the front elastic belt, wherein the distal edge of the front elastic belt matches the distal edge of the back elastic belt.

6. The absorbent article of claim 4, wherein the waist guard portion is provided on the back elastic belt and not on the front elastic belt, wherein the distal edge of the front elastic belt matches the second inner waist fold point of the back elastic belt.

7. The absorbent article of claim 1, wherein the inner sheet of the back elastic belt is a hydrophobic nonwoven layer, the outer sheet of the back elastic belt is a nonwoven layer, and wherein the basis weight of the outer sheet is greater than that of the inner sheet.

8. The absorbent article of claim 1, wherein the outer sheet of the back elastic belt has a plurality of apertures.

* * * * *